United States Patent [19]

Steinmann

[11] Patent Number: 4,916,247

[45] Date of Patent: Apr. 10, 1990

[54] ORGANOMETAL-CONTAINING COMPOUNDS

[75] Inventor: Alfred Steinmann, Praroman, Switzerland

[73] Assignee: Ciba-Geigy Corporation, Ardsley, N.Y.

[21] Appl. No.: 237,473

[22] Filed: Aug. 29, 1988

[30] Foreign Application Priority Data

Sep. 7, 1987 [CH] Switzerland .................. 03425/87

[51] Int. Cl.$^4$ .................. C07F 7/08; C07F 7/04; C07F 7/22; C07F 7/30

[52] U.S. Cl. .................. 556/82; 556/87; 556/88; 556/93; 556/420; 556/430; 556/437; 556/107; 556/440

[58] Field of Search .................. 556/440, 437, 87, 420, 556/82, 31, 9, 12, 430, 93, 88, 107

[56] References Cited

U.S. PATENT DOCUMENTS

| | | | |
|---|---|---|---|
| 2,840,603 | 6/1958 | Mock et al. .................. | 556/107 |
| 3,321,361 | 5/1967 | Mem et al. .................. | 556/87 |
| 3,629,196 | 12/1971 | Hahn et al. .................. | 556/420 |
| 4,481,365 | 11/1984 | Fürster et al. .................. | 556/440 |
| 4,491,628 | 1/1985 | Ito et al. . | |
| 4,689,288 | 8/1987 | Buiguez et al. . | |

OTHER PUBLICATIONS

H. Franke, Appl. Phys. Letters, 45, 110 (1984).
F. Buiguez et al., Microcircuit Eng., 1985, 471.
O.G Notice of 4,443,044.

*Primary Examiner*—Paul F. Shaver
*Assistant Examiner*—Stuart L. Hendrickson
*Attorney, Agent, or Firm*—Luther A. R. Hall

[57] ABSTRACT

Organometal-containing styrene derivatives of the formula I

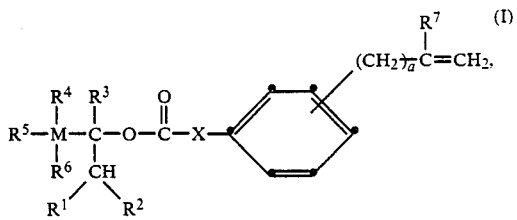

in which, for example, M is Si, X is 0, $R^1$ and $R^2$ are hydrogen, $R^4$ to $R^6$ are each methyl, a is zero and $R^7$ is hydrogen or methyl, and organometal-containing compounds of the formula VII

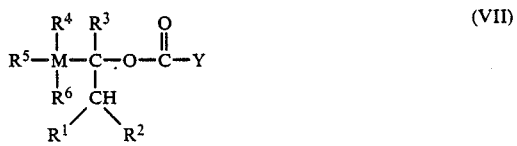

in which M and $R^1$ to $R^6$ are, for example, as defined above and Y is, for example, 4-nitrophenoxy, are valuable starting materials for the preparation of organometal-containing polymers. The polymers are suitable for the preparation of photoresists which can be developed under dry conditions, such as are required in the production of structured images, particularly in microelectronics.

7 Claims, No Drawings

ORGANOMETAL-CONTAINING COMPOUNDS

The invention relates to organometal-containing styrene derivatives, processes for their preparation, the novel carbonyl compounds used for the preparation of the styrene derivatives, and organometal-containing reagents which can be reacted with polymers containing certain functional groups.

As is known, styrene derivatives can be polymerized to give polystyrenes by free-radical, anionic or cationic mechanisms. If polymers of this type contain functional groups which are altered by irradiation, for example split off, they can be employed as resist materials. Thus U.S. Pat. No. 4,491,628 describes resist compositions of matter containing a polymer having side groups which are unstable to acids, for example tert-butyl ester or tert-butyl carbonate groups, and a photoinitiator which generates acid when irradiated. The polymers employed are preferably vinyl polymers, such as polystyrene or polyacrylate, whereas the photoinitiators used are, in particular, onium salts, for example diaryliodonium or triarylsulfonium salts. In the areas exposed to light, acid is generated, the groups unstable to acid are split off and the polarity of the polymer is altered thereby. Both positive and negative images can be produced by means of this photoresist by selecting a suitable polar or non-polar solvent for developing the image.

For many applications, particularly in microelectronics, resists which can be developed by means of solvents do not meet the high requirements. Compositions which can be developed under dry conditions are preferred, i.e. resists containing compounds which, after irradiation, decompose to give volatile particles or which, after irradiation, can be structured by means of a plasma without wet development being required for the production of images. Various materials have been suggested for this purpose, for example polymethyl methacrylate, polyethylene terephthalate, nitrocellulose or polyisoprene [see, for example, H. Franke, Appl. Phys. Lett. 45 (1), 110 et seq (1984)]. If such materials are used, various disadvantages are frequently found, such as low sensitivity, inadequate stability, formation of non-volatile residues, inadequate resistance to oxygen plasma or inadequate resolution.

Polystyrenes having silicon-containing side groups which, together with certain photoinitiators, are suitable for use as positive resists which can be developed under dry conditions are described in EP-A No. 178,208 and in Microcircuit Engineering, 471–481 (1985). In this case trialkylsilyl groups which are attached to the polystyrene chain via ether oxygen atoms or amine nitrogen atoms are split off in the irradiated areas of the resist film. This makes it possible to remove the irradiated areas of the film by means of plasma development whereas the non-irradiated, silicon-containing areas of the film are resistant to plasma. The disadvantage of this system is the relatively high light dosage of 80–120 mJ/cm$^2$ which is required for the production of an image, and also the inadequate solubility of the polymer in suitable solvents. The volatility of the silicon-containing compounds which are split off during irradiation is also not always satisfactory.

U.S. Pat. No. 4,433,044 describes silicon-containing oxime esters of methacrylic acid, the polymers of which can also be employed as positive resists which can be developed under dry conditions and are sensitive in the short-wave UV range. In this case trimethylsilyl groups are attached via methylene bridges directly to the benzene ring of the acetophenone oxime radical of the polymer side chains. However, this system requires a very high light dosage of 1000–4500 mJ/cm$^2$ in order to obtain adequate detachment of the silicon-containing radical. In addition, the system must be heated in a high vacuum at an elevated temperature before the plasma etching process in order to obtain a good image structure.

It has now been found that styrene derivatives containing at least one substituent based on certain silyl, stannyl or germanyl groups can be polymerized to give polymers which, when mixed with catalytic amounts of specific photoinitiators, display a very high sensitivity to radiation.

In addition these polymers are distinguished by a high resistance to oxygen plasma. If it is advantageous, the irradiated polymers can also be developed under wet conditions, it being possible to produce either positive or negative images, depending on the polarity of the developer used. In addition, the compounds which are split off from the polymer side chains and set free during irradiation are readily volatile so that very high temperatures are not required for the dry development, nor even a high vacuum.

The present invention relates to organometal-containing styrene derivatives of the formula I

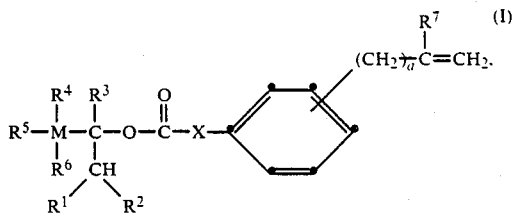

in which $R^1$ to $R^6$ independently of one another are $C_1$–$C_4$alkyl, $C_1$–$C_4$-alkoxy, phenyl, benzyl, phenoxy, a group $-M(R^8)_3$ or

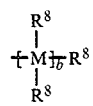

or $R^3$ and $R^4$ together are

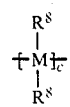

and $R^1$ to $R^3$ can, in addition, also be hydrogen atoms, $R^7$ is hydrogen or $C_1$–$C_4$alkyl and $R^8$ is $C_1$–$C_4$alkyl, $C_1$–$C_4$alkoxy, phenyl, benzyl or phenoxy, M is Si, Ge, Sn, $CH_2Si$ or OSi and X is O, S or NH and a is zero or 1, b is an integer from 1 to 6 and c is an integer from 3 to 6.

The $C_1$–$C_4$alkyl groups or the alkyl radicals of the $C_1$–$C_4$alkoxy groups of the radicals $R^1$ to $R^8$ in the styrene derivatives according to the invention can be branched or, preferably, can be linear; examples are n-, iso-, sec-, or tert-butyl, n-propyl, isopropyl, ethyl and, especially, methyl.

Organometal-containing compounds of the formula I metal which are particularly preferred are silicon compounds in which M is $CH_2Si$, OSi or, especially, Si. Styrene derivatives according to the invention in which X is S or, especially, O are also preferred.

The present styrene derivatives contain, in accordance with the definition, at least one silicon, germanium or tin atom M, but they can also contain two or more of these atoms. If the substituents $R^3$ and $R^4$ together are a divalent radical

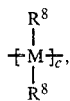

the compounds according to the invention contain, for example, a ring containing one carbon atom and several metal atoms. In this regard compounds having five-membered and six-membered rings are preferred. Compounds according to the invention in which the radicals $R^4$, $R^5$ and $R^6$ are identical are also preferred.

In general, preferred styrene derivatives according to the invention are those which, when irradiated in the presence of an acid-liberating photoinitiator, split off in addition to $CO_2$ a compound I*

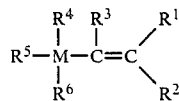

which is as readily volatile as possible. It will readily be understood that this aim is achieved by means of suitable combinations of the substituents $R^1$ to $R^6$ and of the metal atom M.

If one of the radicals $R^1$ to $R^6$ in the compounds according to the invention is

b is preferably an integer from 1 to 3, in particular 1.

Styrene derivatives of the formula I which are also preferred are those in which $R^1$ and $R^2$ are each hydrogen, $R^3$ is methyl or $Si(CH_3)_3$ and $R^4$ to $R^6$ are each methyl or in which $R^3$ and $R^4$ together are

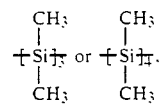

and especially styrene derivatives of the formula I in which $R^1$ and $R^2$ are each hydrogen, $R^3$ is methyl or $Si(CH_3)_3$ and $R^4$ to $R^6$ are each methyl. Compounds of the formula I which are also preferred are those in which a is zero and $R^7$ is hydrogen or methyl.

Compounds of the formula I which are particularly preferred are those in which $R^1$ and $R^2$ are each hydrogen and $R^3$ to $R^6$ are each a methyl group. Styrene derivatives according to the invention which are very particularly preferred are 4-(2'-trimethylsilyl-2'-propoxycarbonyloxy)-styrene, 4-(2'-trimethylsilyl-2'-propoxycarbonyloxy)-α-methylstyrene and 4-(1',1'-bistrimethylsilylethoxycarbonyloxy)-α-methylstyrene.

The styrene derivatives, according to the invention, of the formula I can be prepared either (a) directly by reacting an organometal-containing alcohol of the formula II

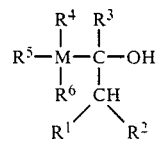

with a chloroformic acid derivative of the formula IIIa

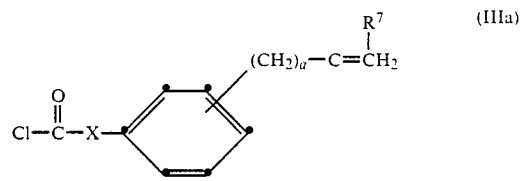

or by reacting an organometal-containing chloroformate of the formula V

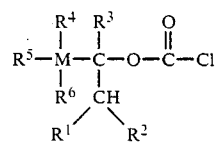

with a compound of the formula VIa

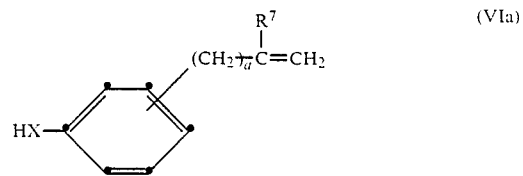

or (b) via the corresponding carbonyl compounds by reacting the organometal-containing alcohol of the formula II, with a chloroformic acid derivative of the formula IIIb

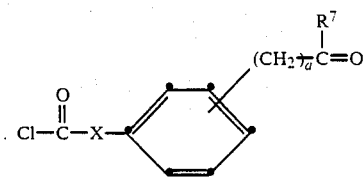

to give the carbonyl compound of the formula IV

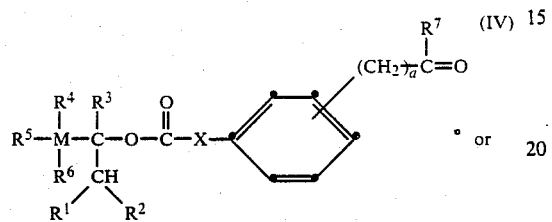

by reacting the organometal-containing chloroformate of the formula V with a compound of the formula VIb

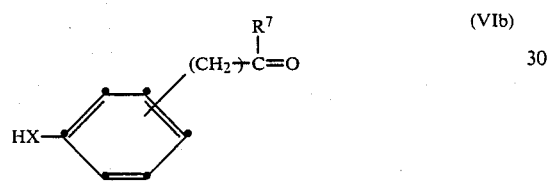

to give the compound of the formula IV and subsequently carrying out a Wittig reaction of the carbonyl compound of the formula IV with a phosphorus ylid, the symbols $R^1$ to $R^7$, M, X and a in the formulae II to VI being as defined in claim 1.

Organometal-containing alcohols of the formula II are known or can be prepared in a known manner. Thus the preparation of a silicon-containing alcohol by reacting triaehylchlorosilane with acetone is described in J. Organomet. Chem. 49 (1973) C9-C12. Organometal-containing alcohols of the formula II can also be prepared as described in J. Org. Chem. 45 (1980) 3571–3578, in Zh. Obshch. Khim. 36 (1966) 1709, in Tetrahedron Lett. 1976, 1591–1594 or in J. Organomet. Chem. 1981 33–47, or in an analogous manner.

Chloroformic acid derivatives of the formula III are also known and can be prepared, for example, by reacting phosgene with a substituted phenol, thiophenol or aniline of the formula VI, preferably in the presence of a base, for example a tertiary amine, such as pyridine or dimethylaniline. Organometal-containing chloroformates of the formula V linked metal can also be synthesized analogously by reacting an alcohol of the formula II with phosgene. A method of preparing chloroformic acid derivatives of the formula IIIa is described, for example, in Angew. Makromol. Chem. 60/61 (1977) 125–137 or German Offenlegungsschrift No. 2,508,512. Chloroformic acid derivatives of the formula IIIa can also be prepared by reacting the corresponding compounds of the formula VIa with phosgene, as described, for example, in German Patent Specification 1,193,031.

A large number of suitable syntheses of chloroformic acid derivatives, for example chloroformates, and reaction products thereof with alcohols, thiols and amines is described, for example, in Chem. Rev. 64 (1964) 645–687.

The compounds of the formula VI are known and, in general, are also commercially available.

The organometal-containing carbonyl compounds of the formula IV have been developed for the preparation of the compounds, according to the invention, of the formula I and thus also form a subject of the invention. They can, for example, be converted into the styrene derivatives of the formula I by means of a Wittig reaction in a known manner by reaction with a phosphorus ylid. Suitable phosphorus ylids can be prepared, for example, by reacting a methyltriarylphosphonium salt, such as methyltriphenylphosphonium bromide with a strong base, such as sodium hydride or potassium tert-butylate. Wittig reactions are described in many reviews, for example in House "Modern Synthetic Reactions", 2nd edition, pages 682–709, W. A. Benjamin Inc., Menlo Park Calif., U.S.A., 1972.

The invention also relates to organometal-containing compounds of the formula VII

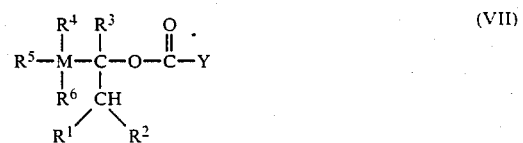

in which $R^1$ to $R^6$ and M are as defined above in Formula I and Y is a detachable group suitable for nucleophilic substitution.

The preferred meaning of the symbols $R^1$ to $R^7$, M, X and a in the compounds, according to the invention, of the formulae IV and VII is identical with the preferred meaning of these symbols in the compounds of the formula I.

The compounds of the formula VII are also valuable starting materials for the preparation of organometal-containing polymers by reacting them, for example, with certain nucleophilic functional groups, such as hydroxyl, mercapto, amino or imino groups, in the polymers and thereby attaching the radical of the formula VII*

as an organometal-containing grouping to the polymer. Examples of polymers suitable for this reaction are polyalcohols and polyphenols, such as polyvinylalcohol, novolaks or poly-4-hydroxystyrene, polythiols or polyimines.

Detachable groups Y which are suitable for nucleophilic substitution are known. The most important requirement in the choice of the detachable group is that it should be less nucleophilic than the functional groups in the polymer with which it is to be reacted.

Detachable groups Y in the compounds of the formula VII which are particularly suitable are phenoxy radicals substituted by electron acceptor groups, or five-membered or six-membered heterocyclic structures containing at least one, preferably two, heteroatoms, for example O, S and especially N atoms, in the ring and which are attached to the carbonyl group in the molecule via one of these heteroatoms. Examples of suitable radicals Y are 1-imidazolyl or a group of the formula VIII

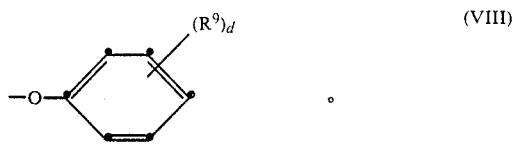

in which $R^9$ is halogen, in particular fluorine, chlorine or bromine, $NO_2$, CN or $CF_3$ and d is an integer from 1 to 5, preferably from 1 to 3. 4-Nitrophenoxy is a particularly suitable radical of the formula VIII.

The compounds of the formula VII can be prepared in a manner known per se, for example by reacting the organometal-containing chloroformates of the formula V with a compound of the formula IX

Another suitable route of synthesis is the reaction of the organometal-containing alcohols of the formula II with a chloroformic acid derivative of the formula X

or with a carbonyl compound of the formula XI

the compounds of the formulae II and V and Y in the formula IX, X and XI being as defined above.

The compounds of the formulae X or XI can be prepared, for example, by reacting phosgene with a compound of the formula IX.

The compounds of the formula IX are known and, in general, are commercially available.

The route of synthesis via compounds of the formula XI in the preparation of compounds of the formula VII is particularly suitable if Y is one of the heterocyclic radicals mentioned above. An example of a suitable compound of the formula XI is 1,1'-carbonyldiimidazole.

As mentioned initially, the compounds according to the invention are valuable starting materials for the preparation of organometal-containing polymers which, when mixed with suitable photoinitiators, can be employed as a resist material which is sensitive to radiation and resistant to plasma and can be developed under dry conditions.

The following Examples illustrate the invention in greater detail.

EXAMPLE 1

2-Trimethylsilyl-2-propanol 83 g (12 mol) of lithium powder are initially placed, under nitrogen, in a 10 l vessel equipped with ground joints and a mechanical stirrer. 6 l of anhydrous THF are added and the mixture is cooled to 0° C. 1500 g (13.8 mol) of trimethylchlorosilane and 313 g (5.4 mol) of acetone are mixed and are added dropwise to the lithium suspension via a dropping funnel. The reaction temperature meanwhile should be 0° C. When the addition is complete, the cooling is removed and the mixture is stirred at 50° C. for 1–2 hours. The solution is separated off from the salt and excess lithium. The residue is washed with n-pentane, and the filtrate is concentrated. In doing so, the solvent is first removed under normal pressure via a metal-coated packed column. The trimethylsilyl ether of 2-trimethylsilyl-2-propanol is then obtained under 20 mbar. 300 g (28%) of a colourless liquid of boiling point 47°–48° C. are obtained.

| $^1$H-NMR (CCl$_4$): | 0 ppm (s, 9H) (H$_3$C)$_3$Si—C |  |
|---|---|---|
|  | 0.1 ppm (s, 9H) (H$_3$C)$_3$Si—O |  |
|  | 1.3 ppm (s, 6H) (H$_3$C)$_2$C |  |
| Elementary analysis: | calculated | found |
| % C | 52.8 | 51.6 |
| % H | 11.8 | 11.7 |

232 g of the trimethylsilylether are dissolved in 900 ml of diethylether, and 700 ml of 15% HCl are added. The 2-phase mixture is heated under reflux, with vigorous stirring, for about one hour. The organic phase is separated off, washed once with water and then thoroughly with sodium bicarbonate solution and dried, and the ether is evaporated off under normal pressure. The residue is distilled under 100 mbar through a packed column. This gives 63 g (65%) of a clear liquid which distills at 65° C. and has a purity, as determined by GC, of over 97%.

| $^1$H-NMR (CCl$_4$): | 0 ppm (s, 9H) (H$_3$C)$_3$Si |  |
|---|---|---|
|  | 1.1 ppm (s, 6H) (H$_3$C)$_2$C |  |
|  | 1.7 ppm (s, 1H) HO— |  |
| Elementary analysis: | calculated | found |
| % C | 54.48 | 54.19 |
| % H | 12.19 | 11.98 |

EXAMPLE 2

4-(2'-Trimethylsilyl-2'-propoxycarbonyloxy)-styrene 244 g (2 of 4-hydroxybenzaldehyde and 2 l of 2M phosgene solution in toluene (4 mol of phosgene) are initially placed, under nitrogen, in a 5 l vessel equipped with ground joints, a mechanical stirrer and a thermometer. 242 g (2 mol) of dimethylaniline are added dropwise at −5° C. When the dropwise addition is complete the mixture is stirred for a further 2 hours at 0° C. It is allowed to warm up to room temperature, the excess phosgene is expelled by means of nitrogen, and the residue is poured into ice water. The organic phase is washed thoroughly with dilute hydrochloric acid and dried with sodium sulfate. The solvent is distilled off on a rotary evaporator. The residue is distilled under a high vacuum. This gives 250 g (68%) of 4-(chlorocarbonyloxy)benzaldehyde, a crystal-clear liquid boiling at 84° C./0.2 mbar. The liquid solidifies on cooling; the melting point is a little above room temperature.

| Elementary analysis: | calculated | found |
|---|---|---|
| % C | 52.06 | 51.07 |
| % H | 2.73 | 2.74 |
| % Cl | 19.21 | 21.26 |

43 g (233 mol) of this chloroformate are dissolved in 30 ml of methylene chloride, and the solution is added dropwise, under nitrogen, to a solution of 30.8 g (233 mmol) of 2-trimethylsilyl-2-propanol and 18.4 g of pyridine (233 mmol) in 120 ml of methylene chloride. The temperature of the solution is kept at $\leq 5°$ C. meanwhile. When the dropwise addition is complete, the mixture is allowed to warm up to room temperature.

After 12 hours under nitrogen it is separated off from salt, and the organic phase is washed with dilute hydrochloric acid, water and sodium bicarbonate solution. After being dried it is freed from solvent. The residue is chromatographed over silica gel using chloroform as the mobile phase. This gives 30.6 g (46%) of 4-(2'-trimethylsilyl-2'-propyloxycarbonyloxy)-benzaldehyde as a colourless liquid.

| $^1$H-NMR (Acetone-d$_6$): | 0.1 ppm (s, 9H) (H$_3$C)$_3$Si |
|---|---|
| | 1.5 ppm (s, 6H) (H$_3$C)$_2$C |
| | 7.3–7.9 ppm (m, 4H) H—Ar. |
| | 10 ppm (s, 1H) CHO |

| Elementary analysis: | calculated | found |
|---|---|---|
| % C | 59.97 | 59.62 |
| % H | 7.19 | 7.18 |
| % Si | 10.01 | 9.95 |

The benzaldehyde derivative is converted into the corresponding styrene derivative by means of a Wittig reaction: 38.6 g (108 mmol) of methyltriphenylphosphonium bromide in 400 ml of anhydrous THF are initially placed in a 1 1 3-necked round-bottomed flask equipped with a dropping funnel and a thermometer. 12.2 g (108 mmol) of potassium tert-butylate are added, and the mixture is stirred under nitrogen for 1 hour at room temperature. 20 g (72 mmol) of the benzaldehyde derivative, dissolved in 180 ml of THF, are then added dropwise at room temperature. After 15 hours thin layer chromatography (1:1 toluene/hexane) indicates only the product. The mixture is poured onto ice and extracted twice with n-hexane. The organic phase is washed twice with water, dried and evaporated. The residue is chromatographed over a silica gel column using 1:1 toluene/hexane. This gives 13 g (65%) of a colourless liquid which can be distilled under high vacuum (boiling point 110° C./0.05 mbar).

| $^1$H-NMR(Acetone-d$_6$): | 0.05 ppm (s, 9H) (H$_3$C)$_3$Si |
|---|---|
| | 1.45 ppm (s, 6H) (H$_3$C)$_2$C |
| | 5.1–5.8 ppm (m, 2H) H$_2$C= |
| | 6.5–6.8 ppm (m, 1H) =CH— |
| | 7.0–7.5 ppm (m, 4H) H—Ar. |

| Elementary analysis: | calculated | found |
|---|---|---|
| % C | 64.71 | 63.95 |
| % H | 7.97 | 7.91 |
| % Si | 10.09 | 10.24 |

EXAMPLE 3

4-(2,-Trimethylsilyl-2'-propoxycarbonyloxy)-α-methylstyrene

This monomer is prepared, starting from 4-hydroxyacetophenone, exactly like the styrene derivative described in Example 2. The yields and the physical data of the compounds prepared are as follows:

4-(Chlorocarbonyloxy)-acetophenone
Yield 82%, melting point 33° C.

$^1$H-NMR (CDCl$_3$):   2.6 ppm (s, 3H) H$_3$C—C(=O)—
7.25–8.10 ppm (m, 4H) H—Ar.

| Elementary analysis: | calculated | found |
|---|---|---|
| % C | 54.43 | 54.41 |
| % H | 3.55 | 3.59 |
| % Cl | 17.85 | 17.78 |

4-(2'-Trimethylsilyl-2'-propoxycarbonyloxy)-acetophenone
Yield 68%, melting point 41° C.

| $^1$H-NMR (Acetone-d$_6$): | 0.1 ppm (s, 9H) (H$_3$C)$_3$Si |
|---|---|
| | 1.5 ppm (s, 6H) (H$_3$C)$_2$C |
| | 2.6 ppm (s, 3H) H$_3$C—C(=O)— |
| | 7.25–8.1 ppm (m, 4H) H—Ar. |

| Elementary analysis: | calculated | found |
|---|---|---|
| % C | 61.19 | 60.90 |
| % H | 7.53 | 7.48 |

4-(2'-Trimethylsilyl-2'-propoxycarbonyloxy)-α-methylstyrene
Yield 53%, boiling point 118° C./0.04 mbar.

| $^1$H-NMR (Acetone-d$_6$): | 0.1 ppm (s, 9H) (H$_3$C)$_3$Si |
|---|---|
| | 1.5 ppm (s, 6H) (H$_3$C)$_2$C |
| | 2.1 ppm (m, 3H) H$_3$C—C=C |
| | 5.1–5.4 ppm (m, 2H) H$_2$C=C< |
| | 7.1–7.6 ppm (m, 4H) H—Ar. |

| Elementary analysis: | calculated | found |
|---|---|---|
| % C | 65.71 | 65.77 |
| % H | 8.27 | 8.30 |

EXAMPLE 4

Poly[4-(2'-trimethylsilyl-2'-propoxycarbonyloxy)-styrene]

10 g (36 mmol) of 4-(2'-trimethylsilyl-2'-propoxycarbonyloxy)-styrene (prepared in accordance with Example 2) are dissolved in 20 ml of toluene, and 1 mol % of 2,2,'-azobisisobutyronitrile is added. The solution is freed from oxygen and polymerized under nitrogen at 70° C. After a few hours the viscous solution is diluted with 50 ml of methylene chloride and poured into 500 ml of methanol. The precipitated polymer is dissolved in methylene chloride again and is reprecipitated in methanol. The polymer is dried in a high vacuum at 50° C. Yield 6 g (60%).

| $^1$H-NMR (CDCl$_3$): | 0.1 ppm (s, 9H) (H$_3$C)$_3$Si |
| --- | --- |
| | 0.75–2.25 (m/s, 9H) —CH$_2$—CH— and (H$_3$C)$_2$C |
| | 6.2–7.1 ppm (m, 4H) H—Ar. |
| Elementary analysis: | calculated | found |
| % C | 64.71 | 64.75 |
| % H | 7.96 | 7.92 |

The molecular weight is determined as $\overline{M}_n = 42{,}000$ and $\overline{M}_w = 87{,}000$ by means of gel permeation chromatography (GPC) in tetrahydrofuran, using polystyrene as standard.

Thermogravimetric analysis: There is a loss in weight of approx. 10% at 160° C. at a heating rate of 4° C./minute in air. At 175° C. the compound is completely decarboxylated. The loss in weight is 55%, which corresponds exactly to the elimination of $CO_2$ and isopropenyltrimethylsilane.

EXAMPLE 5

Poly-[4-(2′-trimethylsilyl-2′-propoxycarbonyloxy)-α-methylstyrene] ·

20 g (68 mmol) of the monomer are dissolved in 60 ml of methylene chloride in 100 ml round-bottomed flask fitted with a glass attachment. Oxygen is removed from the solution, and 1.1 ml of a 1M solution of BF$_3$·Et$_2$O in methylene chloride is added, under nitrogen, at −78° C. Polymerization is carried out at −20° to −40° C. 18 hours later the viscous solution is poured into 1 liter of methanol. The precipitated polymer is separated off, dried and reprecipitated in methylene chloride/methanol. It is then dried in a high vacuum at 50° C. 13 g (65%) of the polymer are obtained.

| $^1$H-NMR (CDCl$_3$): | 0.1 ppm (s, 9H) (CH$_3$)$_3$Si |
| --- | --- |
| | 1.0–2.1 ppm (m/s, 11H) CH$_3$—C, —CH$_2$—, CH$_3$—C—CH$_3$ |
| | 6.4–7.2 ppm (m, 4H) H—Ar. |
| Elementary analysis: | calculated | found |
| % C | 65.71 | 65.73 |
| % H | 8.27 | 8.20 |
| % Si | 9.60 | 9.68 |

GPC measurements in THF indicate an $\overline{M}_n$ of 33,000 and an $\overline{M}_w$ of 84,000.

Thermogravimetric analysis: When heated at a rate of 4° C./minute in air there is a 10% loss in weight at approx. 155° C. and a loss in weight of approx. 53% at 171° C. The 53% loss in weight corresponds to the complete elimination of $CO_2$ and isopropenyltrimethylsilane.

EXAMPLE 6

4-(2′-Trimethylsilyl-2′-propoxycarbonyloxy)-nitrobenzene 10 g (76 mmol) of 2-trimethylsilyl-2-propanol, 6 g (76 mmol) of pyridine and 30 ml of methylene chloride are initially placed, under nitrogen, in a 100 ml glass flask equipped with a thermometer, a dropping funnel and a magnetic stirrer, and the solution is cooled to 0° C. 15.2 g (76 mmol) of 4-nitrophenyl chloroformate are dissolved in 20 ml of methylene chloride and are added dropwise to the above solution at such a rate that the temperature remains between 0° C. and 5° C. When the dropwise addition is complete, the mixture is allowed to warm up to room temperature and is stirred for about another hour. It is poured into ice water, and the organic phase is washed with 1N HCl and then with NaHCO$_3$. After drying, the organic phase is concentrated and the residue is recrystallized from n-hexane. This gives 10 g (44%) of a crystalline substance of melting point 61° C.

| $^1$H-NMR (Acetone-d$_6$): | 0.1 ppm (s, 9H) (H$_3$C)$_3$Si |
| --- | --- |
| | 1.55 ppm (s, 6H) (H$_3$C)$_2$C |
| | 7.4–8.1 ppm (m, 4H) H—Ar. |
| Elementary analysis: | calculated | found |
| % C | 52.51 | 52.31 |
| % H | 6.44 | 6.41 |
| % N | 4.71 | 4.60 |

EXAMPLE 7

1-(2′-Trimethylsilyl-2′-propoxycarbonyl)-imidazole 10 g (76 mmol) of 2-trimethylsilyl-2-propanol, 14.7 g (91 mmol) of 1,1′-carbonyldiimidazole and 50 ml of methylene chloride are initially placed, under nitrogen, in a sulfonation flask equipped with a condenser, a thermometer and a magnetic stirrer. The mixture is then stirred under reflux for 21 hours. It is poured into ice water, the phases are separated and the organic phase is again washed twice with water. The organic phase is dried and concentrated on a rotary evaporator, and the residue is distilled under a high vacuum. This gives 11.3 g (66%) of a colourless liquid of boiling point 90° C./0.1 mbar.

| $^1$H-NMR (Acetone-d$_6$): | 0.2 ppm (s, 9H) (H$_3$C)$_3$Si |
| --- | --- |
| | 1.6 ppm (s, 6H) (H$_3$C)$_2$C |
| | 7.74 und 8.1 ppm (s, 3H) H-Imidazol |
| Elementary analysis: | calculated | found |
| % C | 53.06 | 52.31 |
| % H | 8.02 | 8.02 |
| % N | 12.38 | 12.40 |

EXAMPLE 8

4-(1′,1′-Bistrimethylsilylethoxycarbonyloxy)-α-methylstyrene

The condensation reaction between 4-(chlorocarbonyloxy)-acetophenone and 1,1-bistrimethylsilylethanol (prepared as described in Tetrahedron Lett., 1976, 1591–1594) in methylene chloride is carried out analogously to the condensation described in Example 2. Purification by column chromatography gives a solid which can be recrystallized from hexane. 4-(1′,1′-Bistrimethylsilylethoxycarbonyloxy)-acetophenone Yield 60%, Melting point 79.5° C.

| $^1$H-NMR (CDCl$_3$): | (CH$_3$)$_3$Si (18H, s) | 0.12 ppm |
| --- | --- | --- |
| | CH$_3$—C (3H, s) | 1.6 ppm |
| | CH$_3$—C=O (3H, s) | 2.6 ppm |
| | Aromatic (4H, m) | 7.2–8.05 ppm |
| Elementary analysis: | calculated | found |
| % C | 57.91 | 58.01 |
| % H | 8.01 | 8.13 |
| % Si | 15.93 | 15.92 |

4-(1',1'-Bistrimethylsilylethoxycarbonyloxy)-α-methylstyrene

The Wittig reaction is carried out analogously to Example 2. Purification by column chromatography gives a 41% yield of a colourless liquid.

| $^1$H-NMR (CDCl$_3$): | (CH$_3$)$_3$Si (18H, s) | 0,15 ppm |
| --- | --- | --- |
| | CH$_3$—C (3H, s) | 1,6 ppm |
| | CH$_3$—C= (3H, m) | 2,15 ppm |
| | CH$_2$=C (2H, m) | 5,04–5,33 ppm |
| | Aromatic (4H, m) | 7,00–7,53 ppm |
| Elementary analysis: | calculated | found |
| % C | 61.66 | 61.57 |
| % H | 8.63 | 8.77 |
| % Si | 16.02 | 16.08 |

EXAMPLE 9

Poly-[4-(1',1'-bistrimethylsilylethoxycarbonyloxy)-α-methylstyrene]

20 g (57 mmol) of 4-(1',1'-bisrimethylsilylethoxycarbonyloxy-α-methylstyrene (prepared according to Example 8) are dissolved in 60 ml of anhydrous methylene chloride in a 250 ml round-bottom flask equipped with a magnetic stirrer, and the mixture is freed from oxygen by means of a vacuum/nitrogen line, using the freeze-/thaw technique. The solution is cooled to minus 60° C., and 1.2 mmol of freshly distilled BF$_3$·Et$_2$O are added. Polymerization is carried out for 18 hours between minus 60° C. and minus 40° C. The viscous solution is precipitated in 1 l of methanol. The white polymer powder is dried and dissolved in 100 ml of THF, and the solution is filtered and reprecipitated in 1 l of methanol. The polymer is separated off, sucked dry on the filter in air and dried in a high vacuum at 50° C. Yield: 6.1 g of white polymer powder (31%).

| Elementary analysis: | calculated | found |
| --- | --- | --- |
| % C | 61.66 | 61.60 |
| % H | 8.63 | 8.62 |
| % Si | 16.02 | 16.03 |
| GPC (THF) | $\overline{M}_n$ = 52.000 | |
| | $\overline{M}_w$ = 102.000 | |

Thermogravimetric analysis: The polymer decomposes at 170° C. into CO$_2$ and 1,1-bistrimethylsilylethylene.

EXAMPLE 10

Preparation of 4-(2'-trimethylsilyl-2,'-propoxycarbonyloxy)-α-methylstyrene by reacting 2-trimethylsilyl-2-propanol with 4-chloroformyloxy-α-methylstyrene 10 g (75.6 mmol) of 2-trimethylsilyl-2-propanol and 7.2 g (91 mmol) of pyridine are dissolved in 100 ml of anhydrous methylene chloride in a 250 ml three-necked flask equipped with a dropping funnel and a thermometer. After the solution has been cooled to 0° C., 17.8 g (90.5 mmol) of 4-chloroformyloxy-α-methylstyrene (prepared according to Example 6.2 of German Offenlegungsschrift 2,508,512) are added dropwise. When the drop-wise addition is complete, the mixture is allowed to warm up to room temperature and the suspension is stirred for a further hour. The resulting pyridine hydrochloride is removed and the organic phase is thoroughly washed twice with each of IN HCl, water and saturated sodium bicarbonate solution. It is then dried with sodium sulfate and concentrated on a rotary evaporator. The liquid product is purified over a silica gel column using toluene as the mobile phase. This gives 14 g (40 mmol, 63% yield) of 4-(2'-trimethylsilyl-2'-propoxycarbonyloxy)-α-methylstyrene having properties identical with those of the substance described under Example 3.

USE EXAMPLE

10% by weight of 4-phenylthiophenyldiphenylsulfonium hexafluoroarsenate[prepared as described in J. Polymer Sci., Polymer Chem. Ed., 18, 2677–2695 (1980)], relative to the polymer, are added to a 10% by weight solution of the polymer according to Example 4 in cyclohexanone. This solution is added dropwise through a 0.5 micron filter to a silicon wafer, and a homogeneous film is produced by spin coating. The polymer film is dried for 20 minutes at 90° C. The layer thickness of the amorphous, homogeneous film is 0.5 μm. The film is exposed to light of 254 nm at a dosage of 1–2 mJ/cm$^2$ through a chrome-quartz mask. The exposed material is then developed for 10 minutes at 90° C. The high-resolution mask pattern can be discerned clearly. The exposed zones are etched clear in a reactive ion etching apparatus by means of oxygen plasma under anisotropic conditions (O$_2$ flow: 20 standard cc/minute, pressure: $4 \times 10^{-2}$ mbar, 35 watts), whereas the unexposed zones are not attacked. Measurements showed that the exposed zones are etched about 30 times as fast as unexposed zones. This technique makes it possible to develop under dry conditions even submicron structures in the resist.

What is claimed is:

1. An organometal-containing styrene derivative of the formula I

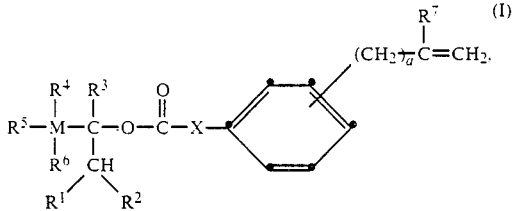

in which $R^1$ to $R^6$ independently of one another are $C_1-C_4$ alkyl $C_1-C_4$-alkoxy, phenyl, benzyl, phenoxy, a group $-M(R^8)_3$ or

or $R^3$ and $R^4$ together are

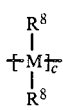

and $R^1$ to $R^3$ can, in addition, also be hydrogen atoms, $R^7$ is hydrogen or $C_1-C_4$alkyl and $R^8$ is $C_1-C_4$alkyl, $C_1-C_4$alkoxy, phenyl, benzyl or phenoxy, M is Si, Ge, Sn, $CH_2Si$ or OSi and X is O,S or NH and a is zero or 1, b is an integer from 1 to 6 and c is an integer from 3 to 6.

2. A styrene derivative according to claim 1, in which M is $CH_2Si$, OSi or Si.

3. A styrene derivative according to claim 1, in which X is S or O.

4. A styrene derivative according to claim 1, in which $R^1$ and $R^2$ are each hydrogen, $R^3$ is methyl or $Si(CH_3)_3$ and $R^4$ to $R^6$ are each methyl or in which $R^3$ and $R^4$ together are

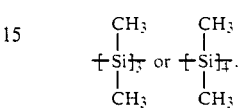

5. A styrene derivative according to claim 4, in which $R^1$ and $R^2$ are each hydrogen, $R^3$ is methyl or $Si(CH_3)_3$ and $R^4$ to $R^6$ are each methyl.

6. A styrene derivative according to claim 1, in which a is zero and $R^7$ is hydrogen or methyl.

7. 4-(2'-Trimethylsilyl-2,'-propoxycarbonyloxy)-styrene, 4-(2,'-trimethylsilyl-2'-propoxycarbonyloxy)-α-methylstyrene and 4-(1',1'-bistrimethylsilylethoxycarbonyloxy)-α-methylstyrene as a compound of the formula I according to claim 1.

* * * * *